(12) United States Patent
Ton (10) Patent No.: US 10,247,965 B2
(45) Date of Patent: Apr. 2, 2019

(54) ERGONOMIC SURGICAL LOUPES

(71) Applicant: Trieu Ton, Elk Grove, CA (US)

(72) Inventor: Trieu Ton, Elk Grove, CA (US)

(*) Notice: Subject to any disclaimer, the term of this patent is extended or adjusted under 35 U.S.C. 154(b) by 0 days.

(21) Appl. No.: 15/728,383

(22) Filed: Oct. 9, 2017

(65) Prior Publication Data

US 2018/0101030 A1    Apr. 12, 2018

Related U.S. Application Data

(60) Provisional application No. 62/405,460, filed on Oct. 7, 2016.

(51) Int. Cl.
| | |
|---|---|
| *G02B 25/00* | (2006.01) |
| *G02C 7/14* | (2006.01) |
| *A61B 90/50* | (2016.01) |
| *G02C 5/04* | (2006.01) |
| *G02C 7/08* | (2006.01) |
| *A61B 90/00* | (2016.01) |

(52) U.S. Cl.
CPC .............. *G02C 7/14* (2013.01); *A61B 90/50* (2016.02); *G02B 25/004* (2013.01); *G02B 25/007* (2013.01); *G02C 5/045* (2013.01); *G02C 7/088* (2013.01); *A61B 2090/3616* (2016.02); *A61B 2090/502* (2016.02)

(58) Field of Classification Search
CPC .............................. G02B 7/002; G02B 25/004
USPC ............... 359/407, 411, 412, 419, 429, 431, 359/480–482; 348/84
See application file for complete search history.

(56) References Cited

U.S. PATENT DOCUMENTS

| | | | | | |
|---|---|---|---|---|---|
| 2,983,183 | A | * | 5/1961 | Pickering | G02B 27/1006 352/67 |
| 5,712,677 | A | * | 1/1998 | Fraering, Jr. | H04N 7/183 348/84 |
| 6,120,145 | A | * | 9/2000 | Lyst, Jr. | G02B 7/002 351/158 |
| 7,242,522 | B2 | * | 7/2007 | Kanai | G02B 25/004 359/407 |
| 7,283,300 | B2 | * | 10/2007 | Jojiki | G02B 7/002 351/158 |
| 8,446,670 | B2 | * | 5/2013 | Woker | G02B 7/002 359/419 |

* cited by examiner

*Primary Examiner* — Audrey Y Chang
(74) *Attorney, Agent, or Firm* — Tod Anthony Kupstas (57) ABSTRACT

An ergonomic surgical loupe consists of a housing, an objective lens, a mirrored Littrow prism, an ocular lens, and an adjustment mechanism. Light travels through the objective lens, is reflected through the Littrow prism, passes through the ocular lens and strikes the user's eye, enabling a 60 degree viewing angle for performing dental work or similar procedures. Occupational strain on the neck and back of the user is reduced by allowing the user to maintain an upright, neutral head and back position while performing work significantly below eye level.

10 Claims, 11 Drawing Sheets

ERGONOMIC SURGICAL LOUPES

The current application claims a priority to the U.S. Provisional Patent application Ser. No. 62/405,460 filed on Oct. 7, 2016. The current application is filed on Oct. 9, 2017, whereas Oct. 7, 2017 and Oct. 8, 2017 were on a weekend.

FIELD OF THE INVENTION

The present invention relates generally to eyewear. More particularly, the present invention relates to ergonomic eyewear for medical professionals.

BACKGROUND OF THE INVENTION

Dentistry is a branch of medicine that consists of the study, diagnosis, prevention, and treatment of diseases, disorders and conditions of the oral cavity, commonly in the dentition but also the oral mucosa, and of adjacent and related structures and tissues, particularly in the maxillofacial (jaw and facial) area.

Although primarily associated with teeth among the general public, the field of dentistry or dental medicine is not limited to teeth but includes other aspects of the craniofacial complex including the temperomandibular and other supporting structures. Dentistry is often also understood to subsume the now largely defunct medical specialty of stomatology (the study of the mouth and its disorders and diseases) for which reason the two terms are used interchangeably in certain regions.

Dentistry is important to one's overall health. Dental treatments are carried out by a dental team, often consisting of a dentist and dental auxiliaries—dental assistants, dental hygienists, dental technicians, as well as dental therapists. Most dentists either work in private practices (primary care), dental hospitals or institutions such as prisons, armed forces bases, and the like (secondary care).

The history of dentistry is almost as ancient as the history of humanity and civilization with the earliest evidence dating from 7000 BC. Remains from the early Harappan periods of the Indus Valley Civilization (c. 3300 BC) show evidence of teeth having been drilled dating back 9,000 years. It is thought that dental surgery was the first specialization from medicine.

When performing dental procedures on a patient, dental practitioners typically assume a standing posture above a patient in a dental chair. The dental practitioner must position their head at a downward angle in order to gain a proper view of the patient and the procedure area. As a result, the neck and back of the practitioner is placed under strain, producing discomfort, pain, and potentially chronic muscular or spinal conditions. To alleviate these conditions, many dentists use loupes.

Generally, a loupe is a simple, small magnification device used to see small details more clearly. Loupes can be very beneficial to dental professionals to enhance surgical precision while performing a procedure. As dental professionals use both hands in performing dental procedures, dental loupes are typically binocular in configuration and typically take the form of a pair of glasses. Some dental loupes are flip-type, which take the form of two small cylinders, one in front of each lens of the glasses. Other types are inset within the lens of the glasses. A typical magnification for use in dentistry is 2.5×, but dental loupes can be anywhere in the range from 2× to 8× magnification. Loupes, in addition to providing viewing magnification, can also improve dentists' posture which can decrease occupational strain. With typical flip down style loupes, the viewing angle for the dentist is about 15 degrees, but the field of view is narrow and far from the pupil. While this is an improvement over not using loupes at all, the individual still needs to tilt their head at an angle to properly view the procedure area. A human head can weigh anywhere from five pounds to 11 pounds, and if kept in a relatively static position for extended period of time, pain will occur. This can decrease career longevity.

It is therefore an objective of the present invention to introduce ergonomic loupes for use in dentistry and other applicable fields that allows the user to maintain their neck and back in a fully upright posture while allowing the user to properly view their surgical working area without having to tilt their head away from the neutral vertical orientation, thus improving the surgeon's ergonomics and prolonging their career.

DETAIL DESCRIPTIONS OF THE INVENTION

All illustrations of the drawings are for the purpose of describing selected versions of the present invention and are not intended to limit the scope of the present invention. The present invention is to be described in detail and is provided in a manner that establishes a thorough understanding of the present invention. There may be aspects of the present invention that may be practiced or utilized without the implementation of some features as they are described. It should be understood that some details have not been described in detail in order to not unnecessarily obscure focus of the invention. References herein to "the preferred embodiment", "one embodiment", "some embodiments", or "alternative embodiments" should be considered to be illustrating aspects of the present invention that may potentially vary in some instances, and should not be considered to be limiting to the scope of the present invention as a whole.

The present invention is a configuration for surgical loupes that is ergonomic and reduces strain on a user's neck while performing an operation. It should be noted that the present invention should not be limited to performing medical or dental surgery on a patient, and may be utilized for other similar situations, such as woodworking, watchmaking, model building, and other types of handiwork. The present invention will allow the user to maintain an upright neck posture and direct their field of view straight forward in relation to their body, while being able to view the subject of the procedure at a downward angle. The present invention will allow the user to be able to see approximately 60 to 90 degrees horizontal without having to angle their head downwards at the working area. This keeps their arms close to their body, neck straight, back straight, and eyes in a comfortable position as they perform dentistry or medical surgery.

It may be understood that portions of the disclosure herein refer to the present invention as a single loupe, but in practice, the present invention may preferably comprise a pair of loupes connected together through a structural connection or by individual connection to a headgear. The fundamental focus of the present invention is on the configuration of an individual loupe that enables the viewing angle of the user to be such that the user may maintain a neutral, upright neck and back posture. Two loupes of said configuration may be utilized in conjunction as is typical with surgical loupes.

Figure 4:
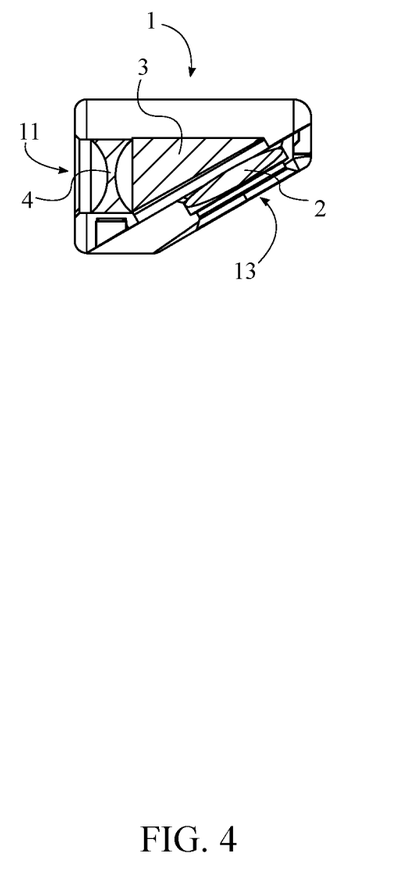
FIG. 4 is a side sectional view along line A-A of FIG. 3.
Figure 5:
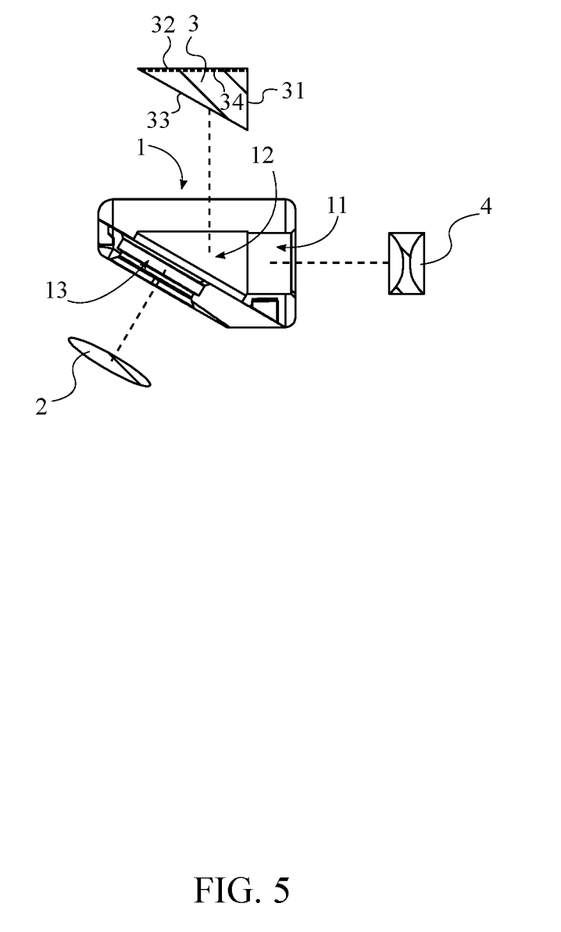
FIG. 5 is an exploded side sectional view along like A-A of FIG. 3.
Figure 6:
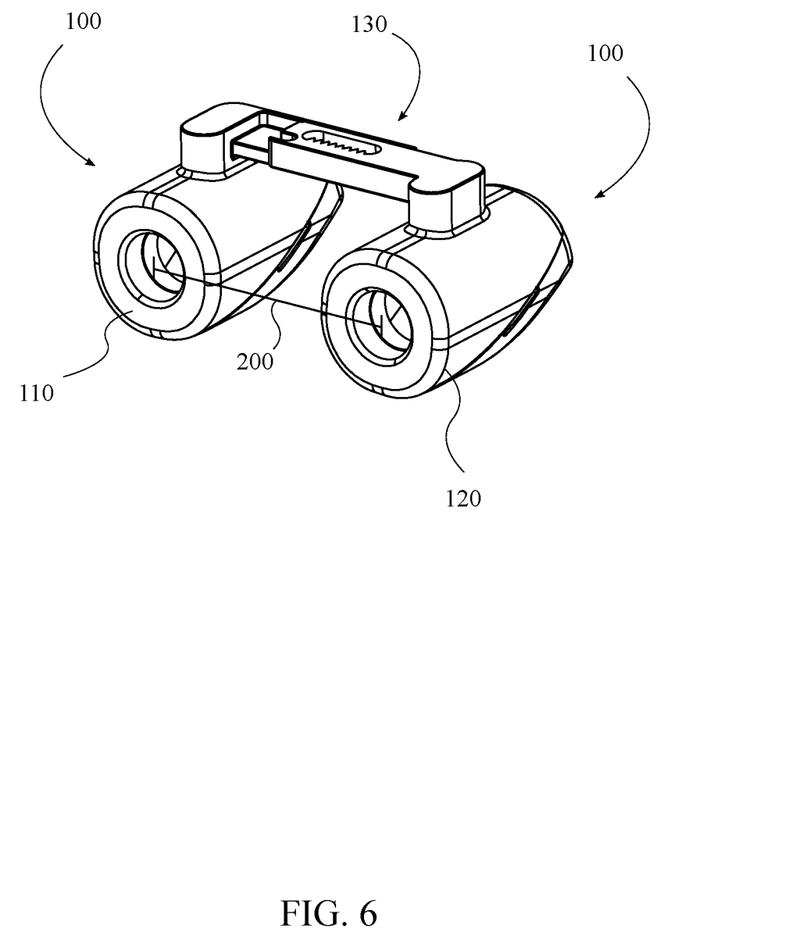
FIG. 6 is a perspective view of a pair of loupes connected to each other.
Figure 7:
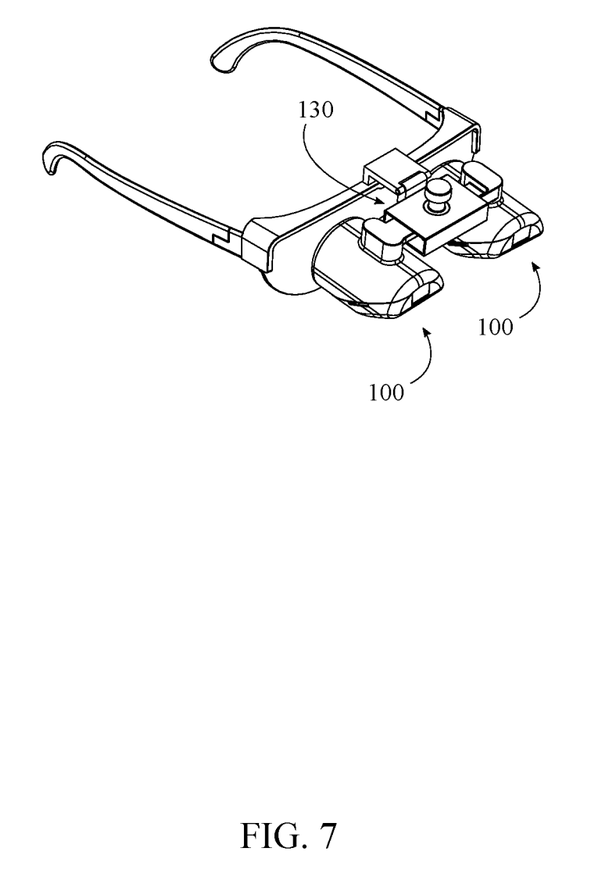
FIG. 7 is a perspective view of a pair of loupes connected to a pair of glasses.

Referring to FIGS. 1-5, in general, the ergonomic surgical loupe of the present invention comprises a housing 1, an objective lens 2, a mirrored Littrow prism 3, an ocular lens 4, and an adjustment mechanism 5. Alternatively, as illustrated in FIG. 6, a set of ergonomic surgical loupes may comprise a pair of loupes 100 and a connection means 130, each of the pair of loupes 100 comprising said housing 1, objective lens 2, mirrored Littrow prism 3, ocular lens 4, and adjustment mechanism 5. The connection means 130 may connect the pair of loupes 100 to each other, with the connection means 130 further connected to a headgear such as an eyeglass frame as shown in FIG. 7, or the connection means 130 may connect each of the pair of loupes 100 independently to the headgear in various embodiments.

The housing 1 is the structural component of the present invention that functions to hold the Littrow prism 3 in place and direct light through the Littrow prism 3 to enable the user to view their subject at a downward angle without tilting their head. Furthermore, the housing 1 may be generally shaped in a triangular configuration, similar to the shape of the Littrow prism 3. The housing 1 may be manufactured through any currently available or new manufacturing process, such as, but not limited to, CNC machining or plastic injection molding, and may be manufactured from any desirable material, such as, but not limited to, various types of plastic, metal, or combinations of materials.

In some embodiments of the present invention, the housing 1 comprises an ocular aperture 11, an interior cavity 12, and an objective aperture 13. The ocular aperture 11 is a viewing aperture through which the user looks in order to utilize the present invention. The objective aperture 13 is the aperture through which light reflected from an object, patient, workspace or other subject on which user desires to perform a procedure traverses into the housing 1 in order to be directed toward the user's eye by the mirrored Littrow prism 3. The interior cavity 12 is a hollow space within the housing 1 that functions to hold the mirrored Littrow prism 3, the ocular lens 4, and the objective lens 2. The ocular aperture 11 and the objective aperture 13 traverse through the housing 1 into the interior cavity 12, and are positioned opposite each other on the housing 1 such that the objective aperture 13 is oriented at an acute viewing angle relative to the ocular aperture 11.

The objective lens 2 is positioned within the interior cavity 12 adjacent to the objective aperture 13. In some embodiments, the objective lens 2 is concentrically aligned with the objective aperture 13. Furthermore, in some embodiments the objective lens 2 is a double convex lens.

Similarly, the ocular lens 4 is positioned within the interior cavity 12 adjacent to the ocular aperture 11, and is concentrically aligned with the ocular aperture 11. In some embodiments, the ocular lens 4 is a double concave lens.

The mirrored Littrow prism 3 is positioned within the interior cavity 12 between the ocular lens 4 and the objective lens 2, wherein the mirrored Littrow prism 3 is configured to redirect light received through the objective aperture 13 by the acute viewing angle towards the ocular aperture 11. In the preferred embodiment, the mirrored Littrow prism 3 is a 30/60/90 triangular prism. In some embodiments, the mirrored Littrow prism 3 may have varying geometry as is desirable or practical in various means of application.

Generally speaking, given that the mirrored Littrow prism 3 is a 30/60/90 triangular prism and that the mirrored Littrow prism 3 is positioned appropriately within the housing 1, the 30 degree angle of the prism is opposite the ocular aperture 11 of the housing 1, the 60 degree angle is opposite the mirrored surface of the prism, and the 90 degree angle is opposite the objective aperture 13 of the housing 1. Thus, in some embodiments, the acute viewing angle at which the ocular aperture 11 and the objective aperture 13 are oriented with respect to each other is 60 degrees.

More specifically, in the preferred embodiment the mirrored Littrow prism 3 comprises a first surface 31, a second surface 32, and a hypotenuse surface 33. The first surface 31 and the second surface 32 are terminally and perpendicularly connected to each other, wherein the first surface 31 and the second surface 32 form a right angle (90 degrees). The hypotenuse surface 33 is terminally connected between the first surface 31 and the second surface 32 opposite the right angle. The first surface 31 is positioned adjacent to the ocular lens 4 opposite the ocular aperture 11, such that the ocular lens 4 is positioned within the housing 1, between the ocular aperture 11 and the first surface 31. Similarly, the hypotenuse surface 33 is positioned adjacent to the objective lens 2 opposite the objective aperture 13, such that the objective lens 2 is positioned between the objective aperture 13 and the hypotenuse surface 33. Furthermore, the second surface 32 comprises a mirrored coating 34. The mirrored coating 34 facilitates proper reflection of light through the mirrored Littrow prism 3.

Figure 8:
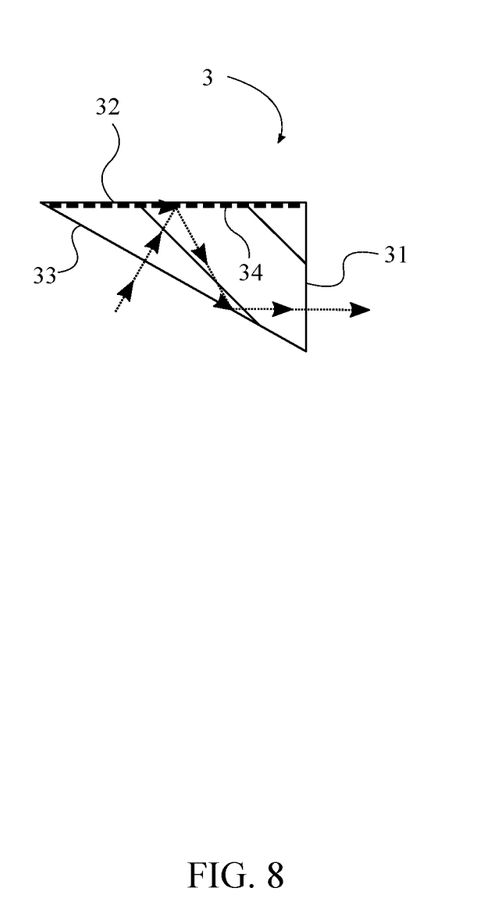
FIG. 8 is an illustration of light passing through the mirrored Littrow prism.

Thus, as illustrated in FIG. 8, light reflected from the patient undergoing the procedure passes through the objective aperture 13, through the objective lens 2, through the hypotenuse surface 33, reflects off the mirrored second surface 32 at a 60 degree angle to the second surface 32, reflects off the interior of the hypotenuse surface 33 at a 30 degree angle, passes through the first surface 31, the objective lens 2, and the objective aperture 13, and finally strikes the user's eye.

The adjustment mechanism 5 may be any useful means for adjusting the loupe in relation to the headgear worn by the user to accommodate varying eye distances, among other factors. The adjustment mechanism 5 should allow the user to move the loupe in relation to the headgear in a horizontal direction (parallel to the eyes), and to rotate each loupe individually. Preferably, the adjustment mechanism 5 is externally connected to the housing 1, such that the adjustment mechanism 5 is configured to adjust the orientation of the housing 1 relative to a headgear. In some embodiments, the loupe is configured to be removably attached to the headgear through the adjustment mechanism 5. Furthermore, the adjustment mechanism 5 is configured to adjust the orientation of the housing 1 relative to the headgear. In some embodiments, a pupillary distance 200 for the viewing of the user (distance between the pupils of the user's eyes, illustrated in FIG. 6) is adjusted by adjusting the orientation of the housing 1 relative to the headgear. In some embodiments, this is accomplished through a horizontal sliding mechanism. In other embodiments, any other viable means of adjusting the pupillary distance 200 may be utilized.

Figure 1:
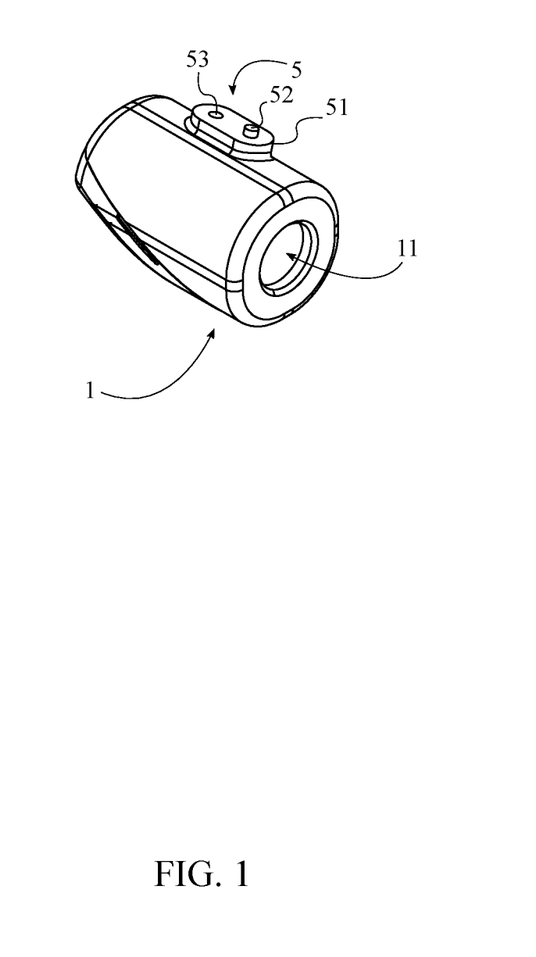
FIG. 1 is an elevated perspective view of one loupe of the present invention.
Figure 2:
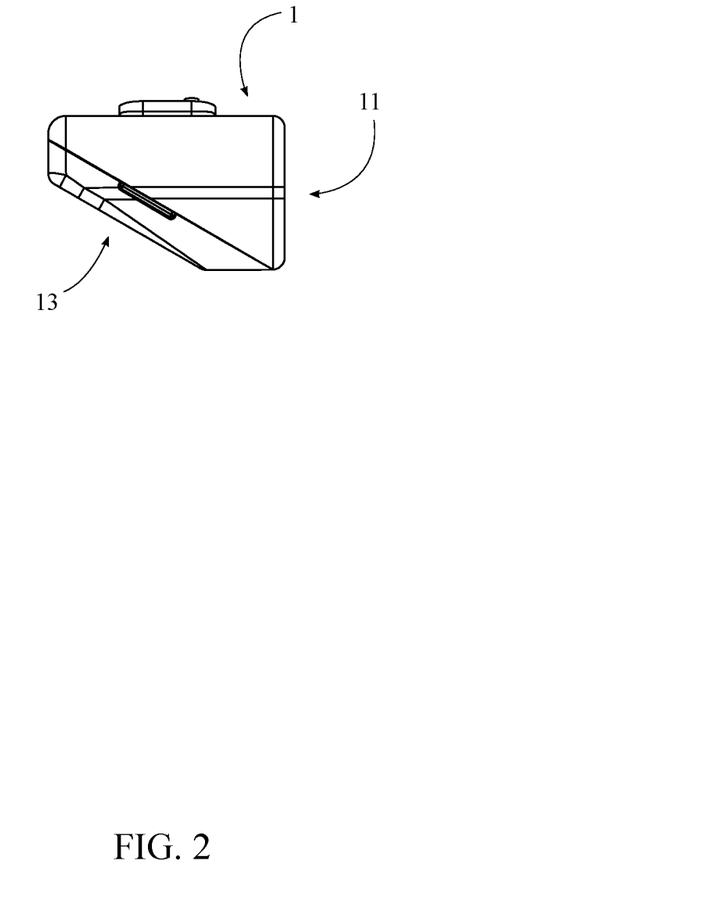
FIG. 2 is a side view of the present invention.
Figure 3:
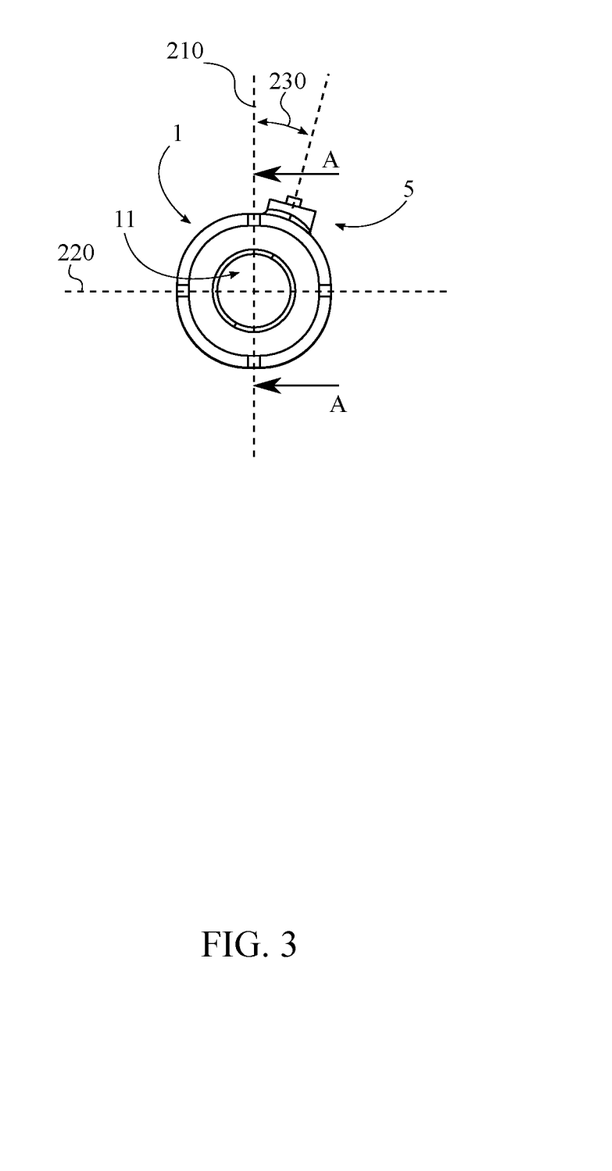
FIG. 3 is a front view of the present invention.

In order to define certain aspects, the housing 1 further comprises a sagittal plane 210 and a transverse plane 220, as shown in FIG. 3. The sagittal plane 210 bisects the ocular aperture 11 and the objective aperture 13, i.e. the sagittal plane 210 is the Y-Z plane of the housing 1. Furthermore, the transverse plane 220 is oriented perpendicular to the sagittal plane 210, and the transverse plane 220 bisects the ocular aperture 11, i.e. the transverse plane 220 is the X-Y plane of the housing 1. Thus, in some embodiments, the adjustment mechanism 5 may be externally connected to the housing 1 at a pupillary convergence angle 230 between the sagittal plane 210 and the transverse plane 220, such as, but not limited to, 5 degrees. The pupillary convergence angle 230 facilitates adequate convergence of focus of the user's eyes on the subject of the procedure.

Figure 9:
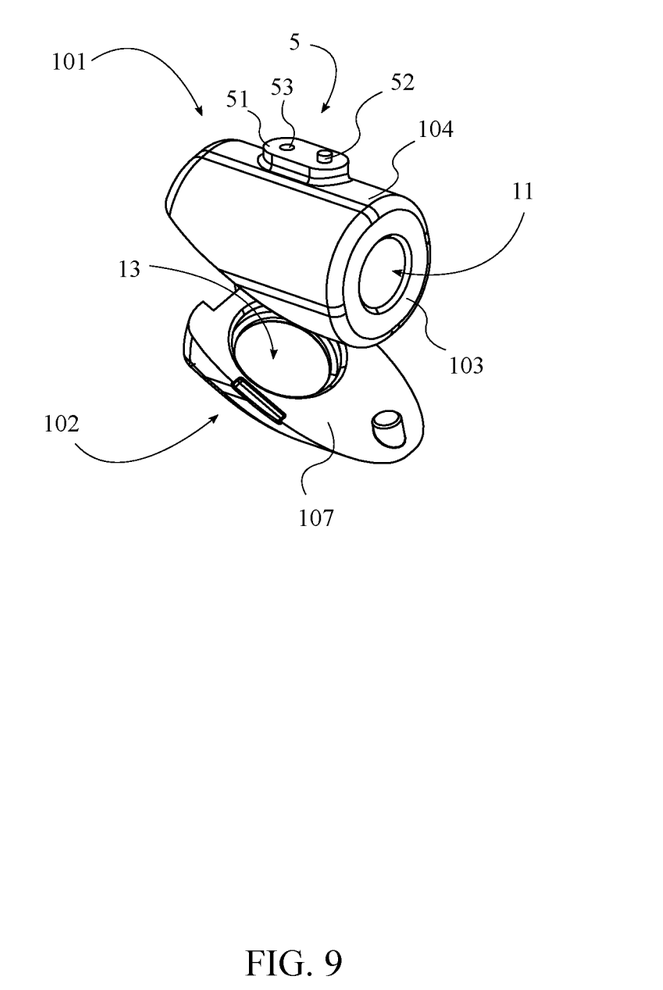
FIG. 9 is a raised perspective exploded view of the housing.
Figure 10:
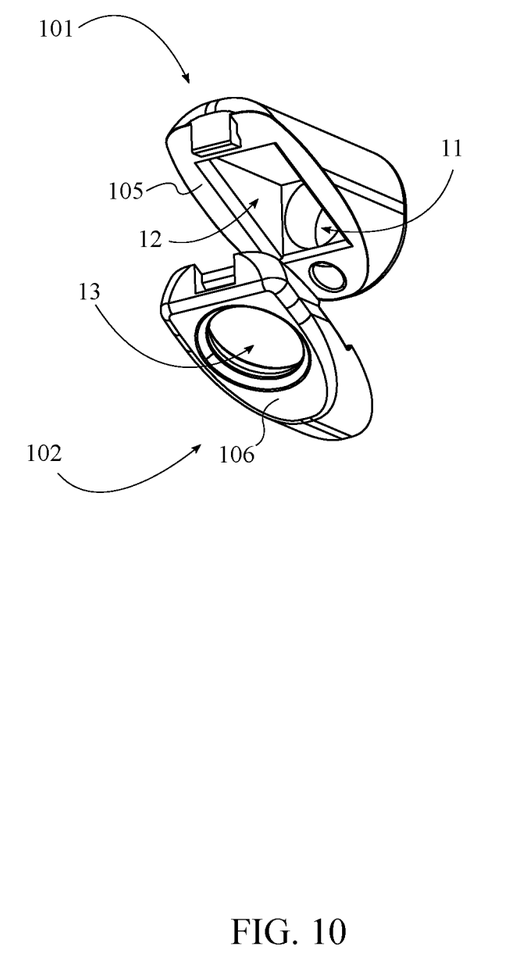
FIG. 10 is a lowered perspective exploded view of the housing.

In some embodiments, the housing 1 is manufactured as a single solid piece. Referring to FIGS. 9-10, in some embodiments, the housing 1 may be constructed of two separate pieces that may be attached together. In such a case, the housing 1 comprises a first housing portion 101 and the second housing portion 102, the first housing portion 101 and the second housing portion 102 being removably attached to each other. Thus, the ocular aperture 11 traverses through the first housing portion 101, and the objective aperture 13 traverses through the second housing portion 102. Moreover, the ocular lens 4 is positioned adjacent to the first housing portion 101, and the objective lens 2 is positioned adjacent to the second housing portion 102. Furthermore, the adjustment mechanism 5 is exernally connected to the first housing portion 101. In some embodiments, the delineation of the housing 1 between the first housing portion 101 and the second housing portion 102 may be generally parallel to the hypotenuse surface 33 of the mirrored Littrow prism 3.

Furthermore, in some embodiments the first housing portion 101 may comprise an ocular surface 103, a top surface 104, and a first connection surface 105, while the second housing portion 102 comprises a viewing surface 106 and a second connection surface 107. The ocular aperture 11 traverses through the ocular surface 103, and the adjustment mechanism 5 is connected to the top surface 104. While the mirrored Littrow prism 3 is positioned within the housing 1, the top surface 104 of the first housing portion 101 is positioned opposite to the second surface 32 of the mirrored Littrow prism 3 through the body of the first housing portion 101, the ocular surface 103 is adjacent to the first surface 31, and the first connection surface 105 is adjacent to the hypotenuse surface 33. The second housing portion 102 is positioned overtop of the hypotenuse surface 33 of the mirrored Littrow prism 3. The objective aperture 13 traverses through the viewing surface 106 and the second connection surface 107, and the first connection surface 105 and the second connection surface 107 are removably attached to each other.

In some embodiments, the adjustment mechanism 5 comprises a base 51, a protrusion 52, and a hole 53. The base 51 is connected to the housing 1, and is oriented at the pupillary convergence angle 230 relative to the sagittal plane 210. The protrusion 52 extends from the base 51, the hole 53 traverses into the base 51, and the protrusion 52 and the hole 53 are separated from each other along the base 51. The protrusion 52 and the hole 53 may be utilized in any applicable manner to be attached to an eyewear in an adjustable fashion. Alternatively, other mechanisms may be utilized as the adjustment mechanism 5. For example, the adjustment mechanism 5 may comprise a first toothed disc, a second toothed disc, and a tightening mechanism, wherein the first toothed disc and the second toothed disc are affixed against each other in a desired angular relation to each other by the tightening mechanism. In general, the adjustment mechanism 5 may be any means of allowing the housing 1 to rotate within a plane defined by the pupillary convergence angle 230.

Figure 11:
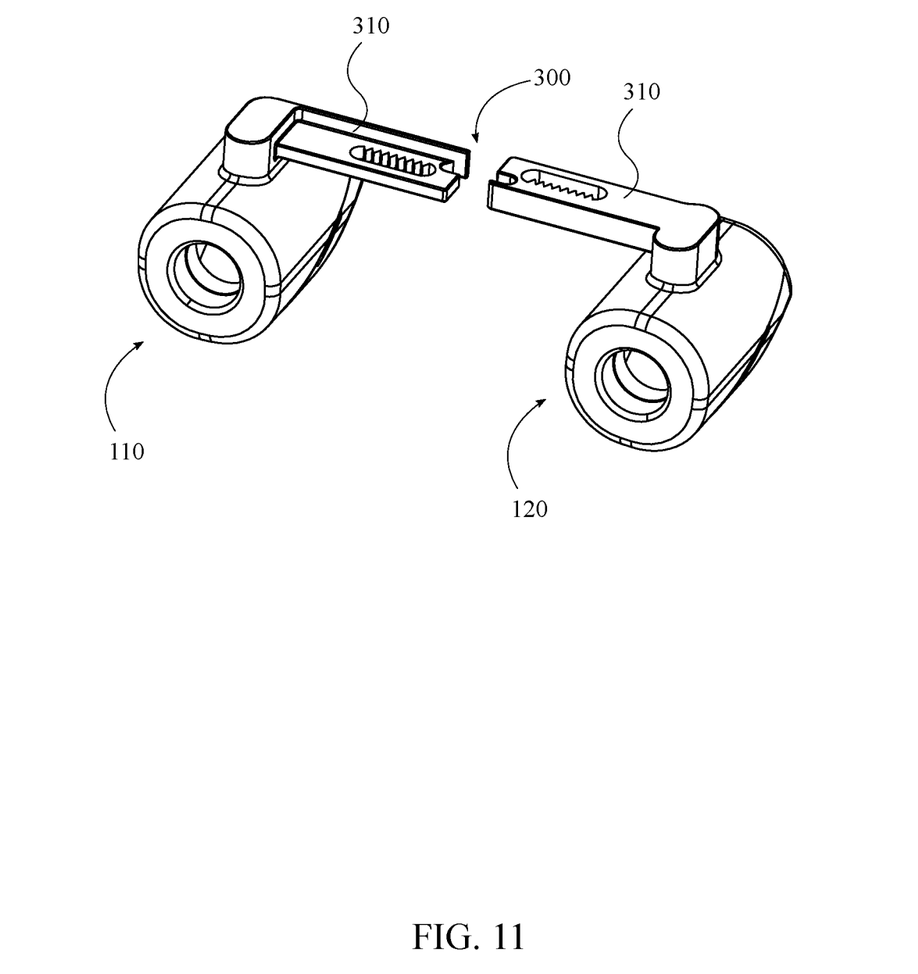
FIG. 11 is an exploded view of a secondary adjustment mechanism showing attachment arms of a pair of loupes.

Referring to FIG. 11, in some embodiments, a secondary adjustment mechanism 300 may function to adjust a linear distance between a first loupe 110 and a second loupe 120. Thus, the secondary adjustment mechanism 300 may comprise an attachment arm 310, with the attachment arm 310 of the first loupe 110 being slidably engaged with the attachment arm 310 of the second loupe 120. It should be noted that the first and second loupe 120 should generally be mirror images of each other. Furthermore, a tightening means, clamping means, or other holding may be utilized to affix the attachment arm 310 of the first loupe 110 and the attachment arm 310 of the second loupe 120 in place relative to each other after a desired distance between the first loupe 110 and the second loupe 120 has been achieved through adjustment of the relative positions of the attachment arms 310 of the first loupe 110 and second loupe 120.

Although the invention has been explained in relation to its preferred embodiment, it is to be understood that many other possible modifications and variations can be made without departing from the spirit and scope of the invention as hereinafter claimed.

What is claimed is:

1. An ergonomic surgical loupe system adapted to provide a 60 degree viewing angle for performing surgery while maintaining head and back position when performing work below eye level comprising:
   a housing;
   an objective lens;
   a single mirrored Littrow prism;
   an ocular lens;
   an adjustment mechanism;
   the housing comprising an ocular aperture, an interior cavity and an objective aperture;
   the ocular aperture and the objective aperture each traversing through the housing into the interior cavity;
   the objective aperture being oriented at an acute viewing angle relative to the ocular aperture;
   the acute viewing angle being 60 degrees;
   the ocular aperture and the objective aperture being positioned opposite each other on the housing;
   the objective lens being a double convex lens;
   the objective lens being concentrically aligned with the objective aperture;
   the objective lens being positioned within the interior cavity adjacent to the objective aperture;
   the ocular lens being a double concave lens;
   the ocular lens being concentrically aligned with the ocular aperture;
   the ocular lens being positioned within the interior cavity adjacent to the ocular aperture;
   the single mirrored Littrow prism being a 30/60/90 triangular prism;
   the single mirrored Littrow prism comprising a first surface, a mirrored second surface, and hypotenuse surface;

the first surface and the mirrored second surface being terminally and perpendicularly connected to each other;

the first surface and the mirrored second surface forming a right angle;

the hypotenuse surface being terminally connected between the first surface and the mirrored second surface opposite the right angle;

the first surface being positioned adjacent to the ocular lens opposite the ocular aperture;

the hypotenuse surface being positioned adjacent to the objective lens opposite the objective aperture;

the single mirrored Littrow prism being positioned within the interior cavity between the ocular lens and the objective lens;

the objective aperture, the objective lens, the hypotenuse surface, the mirrored second surface, the first surface, the ocular lens and the ocular aperture being arranged in such a way that a light passes through the objective aperture, passes through the objective lens, passes through the hypotenuse surface, reflects off the mirrored second surface at a 60 degree angle with respect to the mirrored second surface, reflects off the hypotenuse surface at a 30 degree angle with respect to the hypotenuse surface, passes through the first surface, passes through the ocular lens, and passes through the ocular aperture so as to magnify a right handedness of an image without using any additional prism;

the adjustment mechanism being externally connected to the housing;

the housing comprising a sagittal plane and a transverse plane;

the sagittal plane bisecting the ocular aperture and the objective aperture;

the transverse plane being oriented perpendicular to the sagittal plane;

the transverse plane bisecting the ocular aperture; and the adjustment mechanism being externally connected to the housing at a pupillary convergence angle between the sagittal plane and the transverse plane.

2. The ergonomic surgical loupe system as claimed in claim 1 comprising:

a headgear;

the adjustment mechanism being configured to removably attach the housing to the headgear and; and the adjustment mechanism being configured to adjust an orientation of the housing relative to the headgear.

3. The ergonomic surgical loupe system as claimed in claim 2, comprising:

the headgear being an eyeglass frame.

4. The ergonomic surgical loupe system as claimed in claim 1 comprising:

the pupillary convergence angle being 5 degrees from the sagittal plane.

5. The ergonomic surgical loupe system as claimed in claim 1 comprising:

the housing comprising a first housing portion and a second housing portion; and the first housing portion and the second housing portion being removably attached to each other.

6. The ergonomic surgical loupe system as claimed in claim 5 comprising:

the ocular aperture traversing through the first housing portion; and the objective aperture traversing through the second housing portion.

7. The ergonomic surgical loupe system as claimed in claim 5 comprising:

the adjustment mechanism being externally connected to the first housing portion.

8. The ergonomic surgical loupe system as claimed in claim 5 comprising:

the first housing portion comprising an ocular surface, a top surface and a first connection surface;

the second housing portion comprising a viewing surface and a second connection surface;

the ocular aperture traversing through the ocular surface;

the adjustment mechanism being connected to the top surface;

the objective aperture traversing through the viewing surface and the second connection surface; and the first connection surface and the second connection surface being removably attached to each other.

9. The ergonomic surgical loupe system as claimed in claim 1, comprising:

the adjustment mechanism comprising a base, a protrusion and a hole; the base being connected to the housing;

the base being oriented at the pupillary convergence angle relative to the sagittal plane;

the protrusion extending from the base;

the hole traversing into the base; and the protrusion and the hole being separated from each other along the base.

10. The ergonomic surgical loupe system as claimed in claim 1, wherein the mirrored second surface comprises a mirrored coating, wherein the mirrored coating reflects light towards an interior of the Littrow prism.

* * * * *